United States Patent

Kuroda et al.

[11] Patent Number: 5,443,706
[45] Date of Patent: Aug. 22, 1995

[54] BIOCATALYST-IMMOBILIZED ELECTRODE AND METHOD FOR TREATMENT OF WATER BY USE OF THE ELECTRODE

[75] Inventors: Masao Kuroda, 15-10 Kotobukicho, Ashikaga-shi, Tochigi-ken; Yutaka Sakakibara, Gumma, both of Japan

[73] Assignees: Masao Kuroda, Ashikaga; Yamato Setubi Construction Co., Ltd., Maebashi, both of Japan

[21] Appl. No.: 266,626

[22] Filed: Jun. 28, 1994

Related U.S. Application Data

[62] Division of Ser. No. 54,197, Apr. 30, 1993, Pat. No. 5,360,522.

[30] Foreign Application Priority Data

Jun. 1, 1992 [JP] Japan .................................. 4-163381

[51] Int. Cl.$^6$ .......................... C02F 1/461; C02F 3/00
[52] U.S. Cl. .................................. 204/242; 204/294; 204/403; 204/415; 204/418
[58] Field of Search ............... 204/403, 415, 418, 294, 204/242; 435/817, 288

[56] References Cited

U.S. PATENT DOCUMENTS 4,299,669  11/1981  Obana et al. .................. 204/403
4,820,399   4/1989  Senda et al. .................. 204/403

Primary Examiner—Kathryn Gorgos
Assistant Examiner—Arun S. Phasge
Attorney, Agent, or Firm—Oblon, Spivak, McClelland, Maier, & Neustadt

[57] ABSTRACT

An electrode consists of a cathode matrix material and a biocatalyst immobilized on the matrix material. A water under treatment is treated by disposing the electrode as a cathode and an anode opposed thereto in the water, and applying an electric current between the cathode and the anode.

9 Claims, 3 Drawing Sheets

BIOCATALYST-IMMOBILIZED ELECTRODE AND METHOD FOR TREATMENT OF WATER BY USE OF THE ELECTRODE

This is a division of application Ser. No. 08/054,197 filed on Apr. 30, 1993 now U.S. Pat. No. 5,360,522.

BACKGROUND OF THE INVENTION

1. Field of the Invention

This invention- relates to a biocatalystimmobilized electrode for use in a bioreactor which is useful for producing and recovering useful substances and decomposing environment-polluting substances in water by enhancing the biochemical reaction of a biocatalyst such as a microbial cell body or an enzyme, the electrochemical reaction on the surface of the electrode, and the biochemical reaction of the biocatalyst by the electric current and to a method for the treatment of water by use of the biocatalyst-immobilized electrode.

2. Prior Art Statement

The method which decomposes and removes organic substances and inorganic ions present in water under treatment by feeding the water to a treating column containing an aerobic microbe or anaerobic microbe as a biocatalyst and supplying a substrate (an organic substance as a hydrogen donor or hydrogen) to the treating column and the method which electrolyzes organic substances and inorganic ions present in water under treatment by feeding the water to an electrolytic solution in which an electrode is present and applying an electric current to the electrolytic solution are known to the art.

In the former of the methods mentioned above, when organic substances are supplied, they are required to be in an excess amount for heightening the efficiency of water treatment. This requirement may lead to pollution of the water under treatment by the excess organic substances. When hydrogen is supplied, since hydrogen shows only very low solubility to water and since the reaction proceeds at a rate which is determined by the supply of hydrogen, polluting substances can be thoroughly removed only with extreme difficulty and there is a large possibility of the reaction giving rise to an intermediate which survives treatment for removal.

As the latter method resorting to electrolysis may give rise to secondary products, cannot easily achieve its object.

SUMMARY OF THE INVENTION

This invention has been developed for the purpose of eliminating the problems of the prior art mentioned above.

To be specific, this invention is directed to an electrode consisting essentially of a cathode matrix material and an immobilized biocatalyst and to a method for treating water by preparing an electrode having a biocatalyst immobilized on a cathode matrix, disposing the electrode as a cathode in the water under treatment, opposing an anode thereto in the water, and applying an electric current between the cathode and the anode, thereby inducing a biochemical and an electrochemical reaction of the catalyst.

The above and other features of the invention will become apparent from the following description made with reference to the accompanying drawings.

DESCRIPTION OF THE PREFERRED EMBODIMENT

Figure 1:
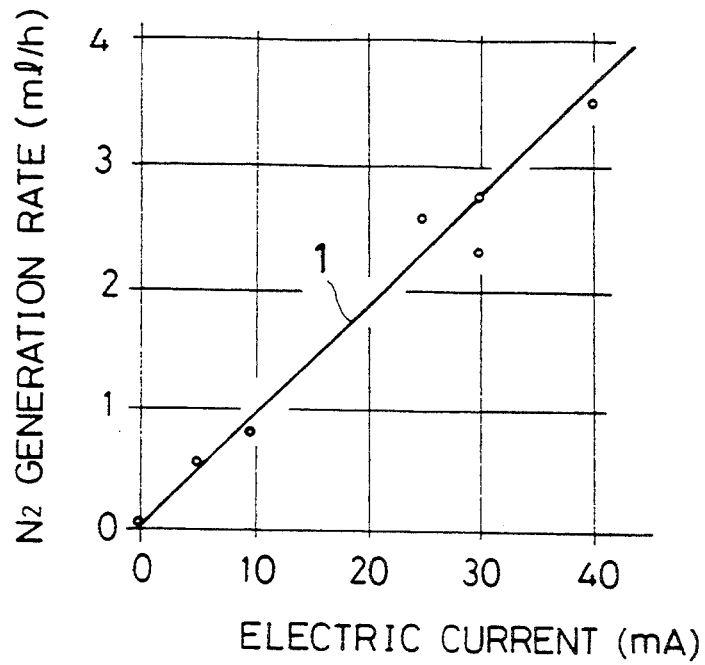
FIG. 1 is a diagram showing the relation between the electric current and the rate of $N_2$ generation in Test Example 1.

The electrode of this invention described above is intended to be used as a cathode for a bioreactor. The matrix material for the electrode is therefore required to be ideally suited to the cathode, excel in electroconductivity and durability, and enable a biocatalyst to be easily immobilized on the surface thereof. A carbonaceous material is preferred.

Since the material for the electrode is destined to have the biocatalyst immobilized on the surface thereof, the surface of this material is desired to be rough or porous so as to facilitate the immobilization. Pretreating the material with plasma increases the adherence between the biocatalyst and the material.

Graphite can be cited as a concrete example of a carbonaceous material.

Though the shape of the electrode is not particularly restricted, a bar, a plate, a film, etc. can be cited as examples of the shape. The cross-sectional shape of the material can be freely selected and may, for example, be that of the letter Y, of a cross, of a star, etc.

The biocatalyst is desired to be immobilized as entrained in a covering material so that when the electrode of this invention is put to actual use, the biocatalyst will not be degraded in activity as by a poisonous substance possibly present in the water under treatment. Materials effectively usable for the covering include dextran, carrageenan, alginic acid and derivatives thereof, polyvinyl alcohol, photolinking resin, urethane, and polyacrylamide gel, for example.

Among the covering materials mentioned above, carrageenan and polyvinyl alcohol prove to be particularly desirable.

One example of the method for effecting the immobilization with the covering comprises suspending given microbial cells in an aqueous polyvinyl alcohol solution, applying the resultant suspension of the microbial cell body to the surface of the electrode, and draining the wet electrode thereby forming a coating of the microbial cells on the electrode.

The biocatalyst can also be immobilized through the medium of a supporting member instead of being directly immobilized on the cathode matrix.

Materials effectively usable for the supporting member herein include woven and non-woven fabrics of natural fibers, synthetic fibers, and carbon fibers, for example.

Though the material for the anode is not particularly restricted, it can be carbon, platinum, or nickel, for example.

When the water under treatment contains $NO_3^-$, the $NO_3^-$ converted into $N_2$ and expelled as such from the water by the following reactions which are induced by applying an electric current to the water.

$$H_2O + e^- \rightarrow \tfrac{1}{2}H_2 + OH^- \qquad (1)$$

$$2NO_3 + 2H^+ + 5H_2 \rightarrow N_2 + 6H_2O \qquad (2)$$

Biocatalysts effectively usable in the present invention include *Paracoccus denitrificans*, *Micrococcus denitrificans*, *Alcaligenous*, *Pseudomonas*, *C. aceticum*, *A. woodii*, *Methanobacterium*, *Enterobacter cloacal*, and sulfuric acid reductases, for example.

For the immobilization of a biocatalyst in the present invention, there can, for example, be used the method which comprises immersing a matrix material for immobilization in a slurry containing the biocatalyst, then adding a substrate in an amount calculated to assume a prescribed concentration therein, and allowing the matrix material to stand for a prescribed period in the slurry thereby enabling the biocatalyst to be immobilized on the matrix material and the method which comprises coating the surface of a matrix material for immobilization with a web of absorbent macromolecular fibers and immersing the coated matrix material in a slurry containing the biocatalyst thereby enabling the biocatalyst to be immobilized thereon.

When the water is treated for denitrification in the present invention, the pH value of the water rises with the progress of the denitrification. In this case, by blowing carbon dioxide gas into the water, the water can be maintained at the level of neutrality which allows the denitrifying microbe to manifest high activity. The increase in the number of immobilized microbial cells is extremely small under no addition of an organic substance. Under addition of an organic substance, about 20% of the consumed organic substance goes to microbial assimilation.

Other uses of the method of the present invention include the following:

1. Formation of $CH_3COOH$ from $CO_2$ and $H_2$ based on the following reactions using *A. woodii*:

$$CO_2 + H_2O \rightarrow HCO_3^- + H^+$$

$$HCO_3^- + H_2 \rightarrow CH_3COOH$$

2. Conversion of hexavalent chromium ion into trivalent chromium ion based on the following reaction using *Enterobacter cloacal*:

$$CrO_4^{2-} + H_2 \rightarrow Cr^{3+}$$

3. Reduction of sulfuric acid ion based on the following reaction using sulfuric acid reductase:

$$SO_4^{2-} + H_2 \rightarrow H_2S$$

4. Formation of $CH_4$ based on the following reaction using *Methanobacterium*:

$$CO_2 + H_2O \rightarrow HCO_2^- + H^+$$

$$HCO_{3hu\ -} + H_2 \rightarrow CH_4$$

The activity of the catalyst-immobilized electrode increases under application of an electric current.

For practical purposes, the amount of this current is in the range of from 0.001 mA to several A.

When the biocatalyst is immobilized in the covered state, the possibility of the activity of the catalyst being degraded by the water under treatment is nil. The covering further prevents microcontamination of the water caused by the product of metabolism of the biocatalyst.

When an organic substance is added as a hydrogen donor as popularly practiced, the organic substance is utilized for the propagation of the biocatalyst. In the case of the treatment for denitrification, for example, the amount of the organic substance thus added is required to be about 2.5 times the stoichiometric amount because the denitrification entails assimilation and metabolism. In the case of the method of this invention, when the water under treatment has a high $NO_3^-$ concentration, the addition of a hydrogen donor can accelerate the speed of denitrification. In the present invention, however, since hydrogen is supplied spontaneously (by electrolysis caused by applying an electric current to the water), the amount of a hydrogen donor to be added is equal to the stoichiometric amount at most, with the result that the propagation of an organic substance is extremely small and no pollution of the water occurs.

Hydrogen donors desirably used in the present invention from the practical point of view include alcohols such as methanol, organic acids such as acetic acid, and hydrocarbons such as dextrose, for example, besides hydrogen.

In the conventional method of electrolysis by applying an electric current to the water, the hydrogen utilization ratio is low because the hydrogen generated by the cathode is diffused in the water where it reacts with oxygen. In contrast in the present invention, the reaction proceeds smoothly and very efficiently because the hydrolysis of the water under treatment induces generation of hydrogen on the surface of the electrode and consequently allows very efficient supply of hydrogen to the biocatalyst. Since this treatment does not require addition of an organic substance, there is no possibility of the water being polluted with an added substance. The treatment can be easily controlled because the hydrogen supply rate can be regulated with the electric current. Further, the electric current enhances the activity of the biocatalyst.

Test Example 1 (Relation between electric current and amount of $N_2$ generated in $NO_3^-$-containing water):

A biomembrane was formed on the surface of a carbon bar measuring 8 mm in diameter and 200 mm in length and having a surface coarseness $\epsilon$ ($\epsilon$ = width of surface irregularities/diameter of electrode) in the range of from 0.01 to 0.1 by immobilizing *Paracoccus denitrificans* by the following method.

The immobilization was effected by immersing the carbon bar in a slurry containing the microbial cells in a concentration of 3,000 mg/liter, adding a substrate ($NANO_3$, acetic acid, etc.) to the slurry in an amount corresponding to a $NO_3^-$ concentration in the range of from 200 to 300 mg/liter, allowing the carbon bar to stand in the slurry for about one month thereby forming a biomembrane on the surface of the carbon bar. Thus an biocatalyst immobilized electrode was obtained.

In a reaction column having an inner volume of about 2,000 cc, the carbon bar having the biocatalyst immobilized as described above was set in place as a cathode and a carbon bar identical in size with the cathode was opposed as an anode to the cathode. To this column, the water under treatment (containing $NO_3^-$ in a concentration of 20 mg/liter) was supplied at the rate of 3 cc/min.

The water under treatment was kept at a temperature of 30° C. and an electric voltage was applied between the opposed electrodes and the amount of electric current was varied, to test for the relation between the magnitude of the electric current and the amount of generated $N_2$. The results of the test are shown by the straight line 1 in FIG. 1. The line 1 indicates that 1 mol of electrons generated 0.1 mol of $N_2$.

Figure 2:
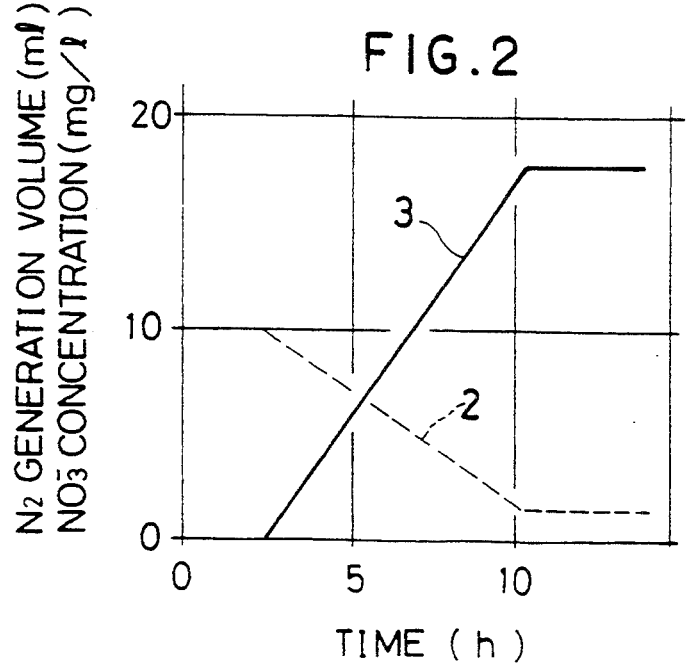
FIG. 2 is a diagram showing the time-course changes in the $NO_3^-$ concentration of the water under treatment and the amount of $N_2$ generation in Test Example 2.

Test Example 2 (Time-course changes of $NO_3^-$ concentration and amount of generated $N_2$):

In the same reaction column as used in Test Example 1, there was placed 2,000 cc of water (containing $NO_3^-$ in a concentration of 10 mg as N per liter). An electric current of 25 mA was passed through the water and the water was maintained at a fixed temperature of 30° C., to test for time-course changes in the $NO_3^-$ content of the water and the amount of generated $N_2$. The results are shown in FIG. 2. The line 2 in FIG. 2 represents the time-course change of $NO_3^-$ content and the line 3 the accumulated amount of generated $N_2$.

EXAMPLE 1

By the same means as shown in Test Example 1, a biomembrane containing a denitrifying microbe was formed in a thickness of about 100 μm on the surface of a carbon bar measuring 8 mm in diameter and 20 cm in length to produce a biocatalyst-immobilized electrode contemplated by this invention.

In a reaction column having an inner volume of about 200 cc, the electrode mentioned above was set in place as a cathode and an anode separately made of carbon was opposed as a counter electrode to the cathode.

A synthetic effluent (containing $NaNO_3$ in a concentration of about 20 mg/liter) was supplied at the rate of 3.3 cc per minute to the reaction column and an electric current was applied to the opposed electrodes in an amount corresponding to a cathode current density of 0.019 $mA/cm^2$. The reaction column was operated continuously for 120 hours under the conditions mentioned above.

The treated water emanating from the reaction column had a $NO_3^-$ content of not more than 1 mg/liter.

EXAMPLE 2

The cathode used in this example comprised a carbon matrix, an approximately 2 mm layer of an aggregate of carbon fibers formed on the carbon matrix by heating rayon fibers to 800° C., and a biocatalyst consisting primarily of methane-producing microbes and acetic acid immobilized to a thickness of about 20 μm on the carbon fiber layer.

This cathode and a carbon anode were disposed in a vessel containing 800 cc of water having a $HCO_3$ content of 1,000 ppm and an electric current was applied between the cathode and anode. The cathode current density was 0.714 $mA/cm^2$ and the temperature of the water 35° C.

Figure 3:
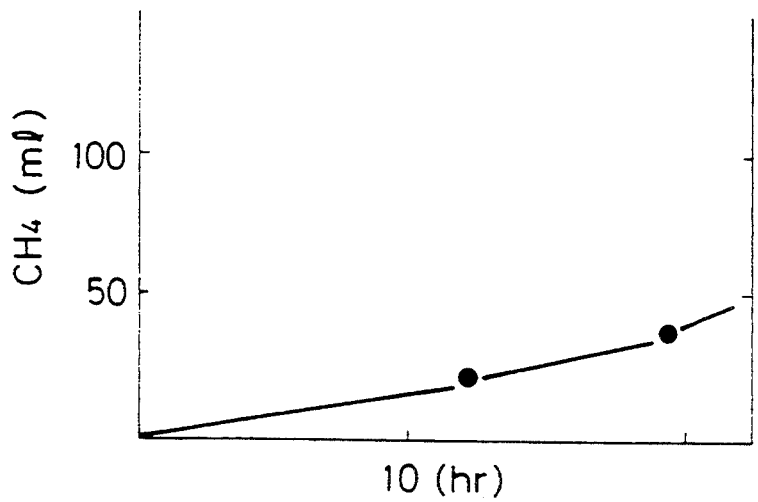
FIG. 3 is a diagram showing the relation between the elapse of time and the amount of methane generated in Example 2.

The time-vs-methane generation relationship is shown in FIG. 3.

EXAMPLE 3

Figure 4:
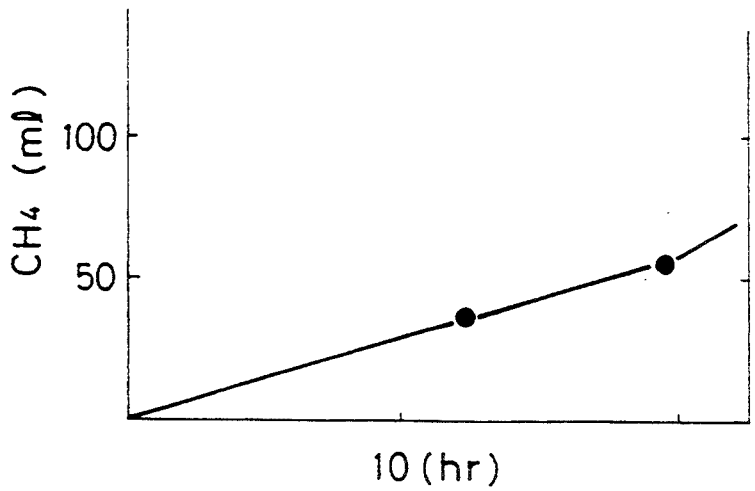
FIG. 4 is a diagram showing the relation between the elapse of time and the amount of methane generated in Example 3.

An operation was carried out by following the procedure of Example 2, except that a macromolecular absorbent material about 2 mm thick and capable of absorbing water and consequently swelling in a gel form was used in the place of the aggregate of carbon fibers. The relation between the elapse of time and the amount of generated methane is shown in FIG. 4.

EXAMPLE 4

A biocatalyst-immobilized electrode according to the present invention was produced by forming a biomembrane containing a methane-producing microbe in a thickness of about 100 μm on a cathode matrix material formed of carbon.

Figure 5:
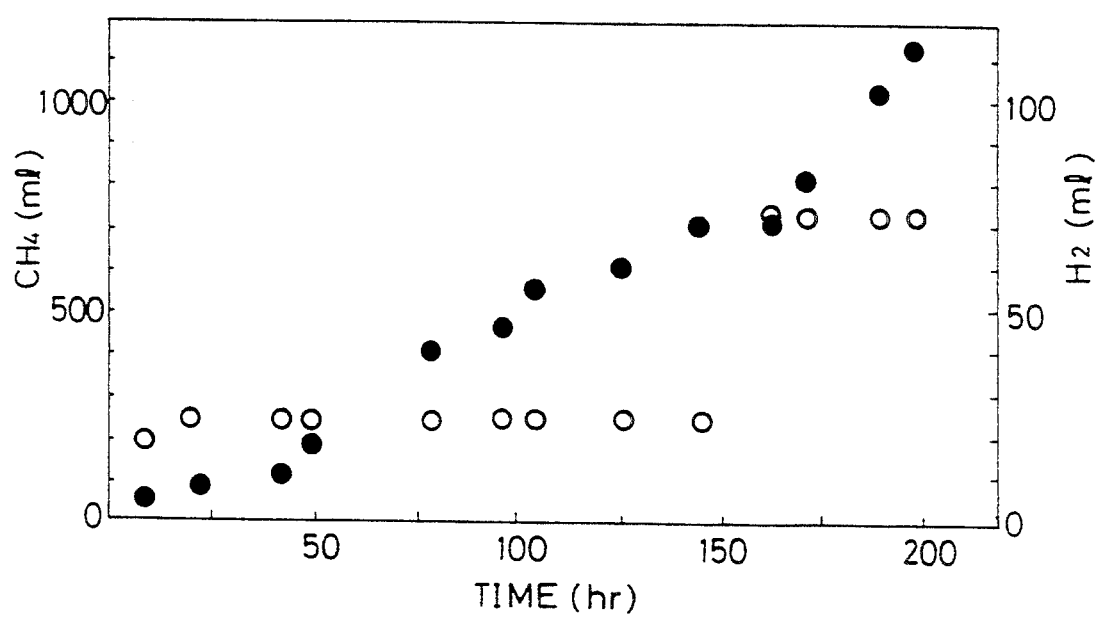
FIG. 5 is a diagram showing the relation between the elapse of time and the amounts of methane and hydrogen generated in Example 4.

In a reaction vessel, the electrode mentioned above was disposed as a cathode and an anode separately made of carbon was opposed to the cathode. Between the cathode and the anode of the reaction vessel supplied with water containing 1,000 ppm of $HCO_3$ and maintained at a temperature of 35° C., an electric current was supplied at a cathode current density of 0.357 $mA/cm^2$ for 100 hours, then at a cathode current density of 0.714 $mA/cm^2$ for 50 hours, and further at a cathode current density of 1.07 $mA/cm^2$ for 50 hours, to test for the amount of $CH_4$ and $H_2$ generated. The results are shown in FIG. 5. In the diagram, the mark ● stands for the amount of $CH_4$ generated and the mark o for the amount of $H_2$ generated.

What is claimed is:

1. An electrode for treating water comprising:
   (i) an electrical conductor; and
   (ii) a biocatalyst which reduces organic substances or inorganic ions immobilized on the surface of said conductor, wherein said biocatalyst uses hydrogen as a reducing agent.

2. The electrode according to claim 1, wherein said biocatalyst reduces inorganic ions.

3. The electrode according to claim 1, wherein said biocatalyst is at least one member selected from the group consisting of *Paracoccus denitrificans, Micrococcus denitrificans, Alcaligenous, Pseudomonas, Clostridium aceticum, Acetobacterium woodii, Methanobacterium, Enterobacter cloacal*, and sulfuric acid reductases.

4. The electrode of claim 1, wherein said electrical conductor is carbonaceous.

5. The electrode of claim 4, wherein said carbonaceous electrical conductor is porous.

6. A device for treating water comprising:
   (a) an electricity source;
   (b) a cathode electrode comprising:
      (i) an electrical conductor of porous carbonaceous material; and
      (ii) a biocatalyst which reduces organic substances or inorganic ions immobilized on a surface of said electrical conductor; and
   (c) an anode electrode;
   wherein when said anode and cathode electrodes are immersed in a water sample and a voltage is applied from said electrical conductor between said cathode electrode and said anode electrode, hydrogen is generated at the surface of said cathode electrode.

7. The device according to claim 26, wherein said biocatalyst uses hydrogen as a reducing agent.

8. The device according to claim 6, wherein said biocatalyst reduces inorganic ions.

9. The device according to claim 6, wherein said biocatalyst is at least one member selected from the group consisting of *Paracoccus denitrificans, Micrococcus denitrificans, Alcaligenous, Pseudomonas, Clostridium aceticum, Acetobacterium woodii, Methanobacterium, Enterobacter cloacal*, and sulfuric acid reductases.

* * * * *